United States Patent [19]

Kodera

[11] Patent Number: 5,093,122
[45] Date of Patent: Mar. 3, 1992

[54] METHOD FOR PREPARING AN S-ALLYLCYSTEINE-CONTAINING COMPOSITION

[75] Inventor: Yukihiro Kodera, Hiroshima, Japan

[73] Assignee: Wakunaga Seiyaku Kabushiki Kaisha, Osaka, Japan

[21] Appl. No.: 616,598

[22] Filed: Nov. 21, 1990

[30] Foreign Application Priority Data

Nov. 22, 1989 [JP] Japan ................................ 1-304358

[51] Int. Cl.$^5$ ................... C12P 11/00; A61K 31/195; C13P 18/04
[52] U.S. Cl. ............................... 424/195.1; 426/535; 435/106; 514/562
[58] Field of Search ....................... 435/106; 426/535; 424/195.1; 514/562

[56] References Cited

PUBLICATIONS

Chemical Abstracts, vol. 111, No. 3, 17th Jul. 1989, p. 514, abstract no. 22380m, Columbus, Ohio, U.S.; T. H. Yu et al.: "Effects of L-cysteine Addition and Pectinolvtic Enzymes Treatment on the Formation of Volatile Compound of Garlic", & Ching-Kuo Nung Yei, Hua Hsueh Hui Chih 1988, 26(4), 406–12 *whole abstract.
World Patent Index (Latest), accession No. 87-040925 [06], Derwent Publications Ltd., London, GB; & JP-A-62 000 423 *whole abstract*.
World Patent Index (Latest), accession No. 82-31661E [16], Derwent Publications Ltd. London, GB; & JP-A-57 042 620 *whole abstract*.
Biotech Abs. 85-0543 Kyriakides et al., PY TCAS Phytochemistry (1985) 24, 3, 600–01.
C.A. 112:196844b Ueda et al., Agric Biol. Chem., 1990, 54(1) 163–9.
C.A. 109:36652x Sano et al., JP62 289193, 16 Dec. 1987.
C.A. 111:22380m Yu et al, 1988, 26(4) 406–12, Chung-kuo Nung Yeh.

*Primary Examiner*—Herbert J. Lilling
*Attorney, Agent, or Firm*—Oblon, Spivak, McClelland, Maier & Neustadt

[57] ABSTRACT

An Allium genus plant, typically garlic is extracted by adding water or alcohol to the garlic, subjecting a mixture of the solvent and the garlic to extraction, and collecting an extract liquid. A composition containing S-allylcysteine in the extract liquid from the garlic is obtained by adding cysteine to the solvent, the mixture of the solvent and the plant under extraction, or the extract liquid collected, and causing the cysteine to convert into S-allylcysteine which is effective controlling hepatopathy and oncogenesis.

7 Claims, 4 Drawing Sheets

METHOD FOR PREPARING AN S-ALLYLCYSTEINE-CONTAINING COMPOSITION

This invention relates to a method for preparing an S-allylcysteine-containing composition from an Allium genus plant, and more particularly, to a method for preparing a composition containing S-allylcysteine in an extract from an Allium genus plant. The composition is useful as an ingredient or additive for medical preparations, cosmetic preparations, foods and the like.

BACKGROUND OF THE INVENTION

Allium genus plants include garlic, elephant garlic, scallion, onion, spring onion, green onion, leek, chives, and the like, and all have specific flavor. Since the ancient days, they have been cultivated all over the world as vegetables or medicinal plants. Among others, garlic is a perennial plant which is grown in Chine, Korea, Japan and many other countries. It is generally known as a tonic or restorative drug and has long been used as stomachic, diuretic, expectorant, intestinal controlling, bactericidal, and anthelmintic agents. There are many reports on characteristic sulfur components of garlic such as allicin, diallylsulfide, S-allylcysteine, ajoene, etc. Recent researches on the pharmaceutical action of these components are reported in the literature and patents, for example, Lancet, 1, 8212, 150–151 (1982), and Japanese Patent Application Kokai Nos. 42967/1980, 5203/1981, 209218/1982, 140526/1986. Among others, S-allylcysteine has been reported as effective in controlling hepatopathy (Hiroshima, Journal of Medical Sciences, 34, 3, 303–309 (1985)), in protecting against radiation (Z. Naturforsch, 35 c, 726 (1980)), and in controlling oncogenesis (Proceedings of the American Association for Cancer Research, 30, 181 (1989)). Practical application of S-allylcysteine is expected. Also, elephant garlic is grown in Japan, U.S., and other countries and widely used like garlic. It was recently reported that elephant garlic contains steroid saponins having antibacterial action (see Chem. Pharm. Bull., 36, 3480–3486 (1988) and Japanese Patent Application Kokai No. 224396/1989). Regarding the treatments, typically deodorizing treatment of garlic and analogues, a number of reports have been available.

However, in the production of a composition rich in a selected component derived from an Allium genus plant, few methods are known except for ajoene derived from garlic (see Japanese Patent Application Kokai No. 129224/1987). No method for producing an S-allylcysteine rich composition is known.

SUMMARY OF THE INVENTION

An object of the present invention is to produce a composition containing a high content of S-allylcysteine in an extract from an Allium genus plant through simple operation at low cost.

The inventors have found that the content of S-allylcysteine in an extract liquid from an Allium genus plant can be substantially increased by adding cysteine in any of the steps of extracting the Allium genus plant with a solvent. Although the reason why the content of S-allylcysteine can be increased by adding cysteine is not well understood, we presume that the enzymatic action of alliin (S-allylcysteine sulfoxide), which is a sulfur-containing amino acid, in the Allium genus plant produces allicin which reacts with the cysteine added to convert the cysteine into S-allylcysteine.

Therefore, the present invention provides a method for preparing an extract liquid from an Allium genus plant, comprising the steps of adding a polar solvent to an Allium genus plant, subjecting a mixture of the solvent and the plant to extraction, and collecting an extract liquid. According to the present invention, cysteine is added to the polar solvent, the mixture of the solvent and the plant under extraction, or the extract liquid collected. Then the cysteine is converted into S-allylcysteine. There is obtained a composition containing S-allylcysteine in the polar solvent extract from the Allium genus plant.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE INVENTION

Figure 1:
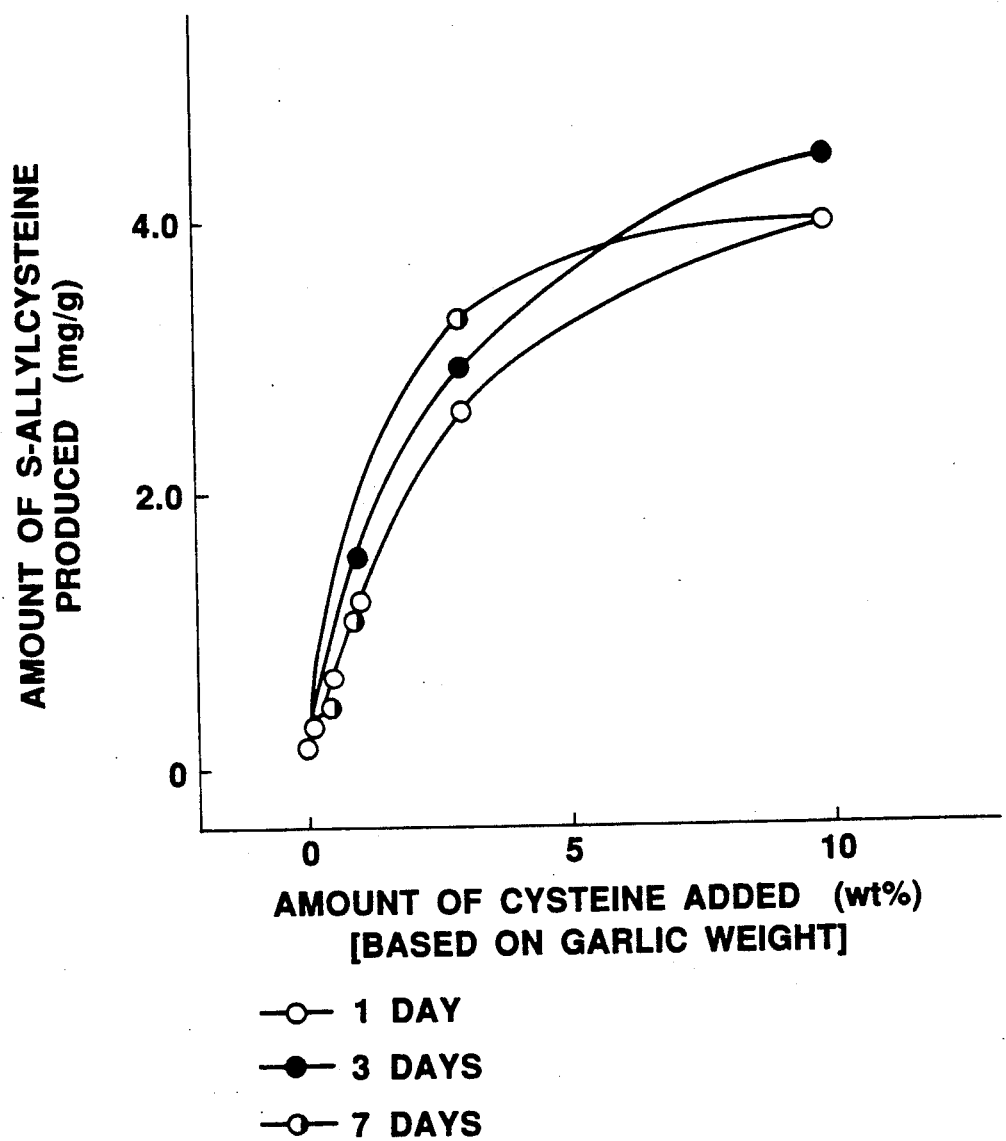
FIG. 1 is a diagram showing the amount of S-allylcysteine produced from garlic versus the amount of cysteine added.

The method for preparing an S-allylcysteine-containing composition according to the present invention starts with an Allium genus plant. The Allium genus plants used herein include plants belonging to the Allium genus of the Liliaceae family, for example,

*Allium sativum L. forma pekinense Makino* commonly known as garlic,

*Allium cepa* commonly known as onion,

*Allium chinense* commonly known as scallion, and

*Allium ampeloprasum* commonly known as great headed garlic or elephant garlic. Garlic and elephant garlic are preferred Allium genus plants. The Allium genus plants may be used alone or in admixture of two or more.

A portion of the plant from which the end product is obtained is preferably a bulb which may be used in raw form although dry or frozen form is acceptable. In processing steps, the bulb may be used as such although crushing is preferred for efficient extraction. It is also possible to use a culture product obtained by subjecting the plant to tissue culture in a conventional manner.

According to the present invention, the plant in any desired form as described above is subjected to extraction. Extraction may be carried out by any conventional techniques commonly used in the extraction of crude drugs.

The extracting solvent used herein is a polar solvent. Often extraction is carried out with water and monohydric lower aliphatic alcohols. The preferred lower alcohols used as the extracting solvent are hydrous or anhydrous alcohols having 1 to 3 carbon atoms, most preferably ethanol. The solvent may be used alone or in admixture of two or more. In the case of a hydrous alcohol, it may have any desired content of alcohol, typically contain 0 to 50% by weight of alcohol. The amount of the extracting solvent used is not particularly limited although the weight of the solvent used is preferably 0.1 to 10 times, more preferably 0.5 to 5 times the weight of the plant.

Extraction may be effected at room temperature or elevated temperatures. Since it takes a long time at room temperature, it is desired to process the mixture of the plant and the solvent at a temperature of 30° to 50° C. for several hours to several days.

At the end of extraction, the solid matter is removed from the extract mixture by suitable separation techniques such as filtration and centrifugal separation, collecting the extract liquid. This extract liquid typically contains sulfur-containing amino acids, polysaccharides, water-soluble components, and fat-soluble sulfides as major components.

According to the present invention, cysteine is added at any stage of the above-mentioned extraction process. More particularly, cysteine may be added to the extracting solvent. Then cysteine is contained in the extracting mixture from the start of extraction. Also, cysteine may be added to the extracting mixture at an intermediate stage of extraction. Alternatively, cysteine may be added to the extract liquid resulting from extraction. In this way, cysteine can be added at any stage of the extraction process. Preferably, cysteine is added to the extract liquid resulting from extraction. The amount of cysteine added preferably ranges from 0.1 to 20%, more preferably from 1 to 5% by weight based on the weight of the plant.

The cysteine added converts into S-allylcysteine in the extract liquid. This reaction can be promoted by maintaining the extract liquid neutral or alkaline, preferably at pH 7-12, more preferably pH 8-10. For pH adjustment, any of commonly used basic or acidic substances may be used if desired. Such pH adjusting substances include sodium hydroxide, aqueous ammonia, hydrochloric acid, acetic acid, and citric acid. The pH adjustment is not essential for the present process and may be carried out at any stage of the process. Preferably, the extract liquid resulting from extraction is subject to pH adjustment. It is possible to carry out extraction in the above-defined pH range if extraction is not adversely affected, so that there is obtained an extract liquid having the desired pH value. Preferably, cysteine is added immediately after pH adjustment. Of course, it is possible to extract an Allium genus plant with a solvent having cysteine already added thereto, and thereafter adjust the pH of the resulting cysteine-containing extract liquid.

The reaction of cysteine may be effected by agitating the extract liquid at room temperature to 50° C., preferably 30° to 50° C. The reaction time, after the addition of cysteine, generally ranges from 1 to 10 days, preferably from 1 to 5 days at a temperature of 30° to 50° C. A longer reaction time will be necessary at room temperature.

At the end of reaction of cysteine, the extracting solvent may be removed. The extract liquid is ready for use without removing the extracting solvent if the solvent is not detrimental.

The resulting composition is the (polar solvent) extract liquid of the Allium genus plant that contains a relatively high concentration of S-allylcysteine which has been converted from cysteine through reaction in the extract liquid. The concentration of S-allylcysteine is generally 0.1 to 3%, preferably 0.5 to 3% by weight based on the weight of the composition from which the extracting solvent has been removed.

Consequently, with only a simple step of adding cysteine, the present invention can efficiently produce an Allium genus plant-derived composition containing a relatively high concentration of S-allylcysteine which is effective in controlling hepatopathy, protecting against radiation and controlling oncogenesis. Thus the present invention greatly contributes to the supply of medicinal, cosmetic and food stock materials.

EXAMPLE

Examples of the present invention are given below by way of illustration and not bay way of limitation.

EXAMPLE 1

To 100 grams of frozen garlic was added 300 ml of water. The mixture was homogenized for about 3 minutes in a blender. The mixture was passed through a gauze filter and the filtrate was adjusted to pH 9.1 using 6 N NaOH. Test tubes were charged with 10 ml portions of the pH adjusted filtrate, to which 0, 2.5, 10, 25, 75 and 250 mg of cysteine were added. The contents were fully agitated. The test tubes were closed with plugs and allowed to stand at 37° C. for several days. Samples were taken out after 1, 3 and 7 days from the cysteine addition. The amount of S-allylcysteine produced was quantitatively determined by high-pressure liquid chromatography (HPLC) using a post column method.

The results are shown in FIG. 1.

EXAMPLE 2

To 159 grams of frozen garlic was added 476 ml of water. The mixture was homogenized for about 3 minutes in a blender. The mixture was passed through a gauze filter and the filtrate was adjusted to pH 9.0 using 6 N NaOH. The pH adjusted filtrate was divided into four portions. One portion is a control. To the three portions, 2.5 mg/ml of cysteine was added immediately after the pH adjustment (0 day), and after 1 and 2 days from the pH adjustment. The portions were allowed to stand at 37° C. for several days. Samples were taken out of each portion after 1, 2, 3 and 4 days from the cysteine addition. The amount of S-allylcysteine produced was quantitatively determined by HPLC using a post column method.

Figure 2:
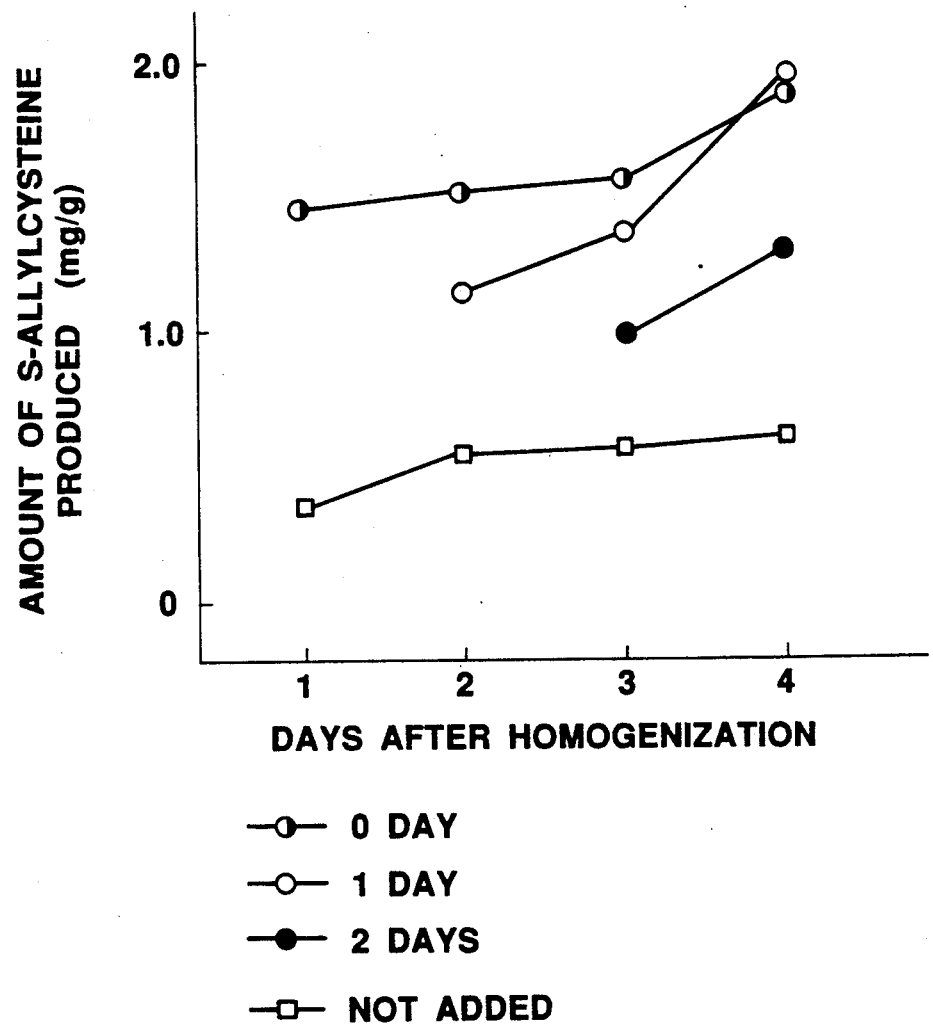
FIG. 2 is a diagram showing the amount of S-allylcysteine produced from garlic versus the cysteine adding stage.

The results are shown in FIG. 2.

EXAMPLE 3

To about 60 grams of frozen garlic were added a three times weight of water and 5%, 10%, 20% and 50% ethanol. Each mixture was homogenized for about 3 minutes in a blender. Each mixture was passed through a gauze filter. Test tubes were charged with 10 ml of the filtrates, to each of which 25 mg of cysteine was added. The contents were fully agitated. The test tubes were closed with plugs and allowed to stand at 37° C. for several days. Samples were taken out after 1, 3 and 7 days from the cysteine addition. The amount of S-allylcysteine produced was quantitatively determined by HPLC using a post column method.

Figure 3:
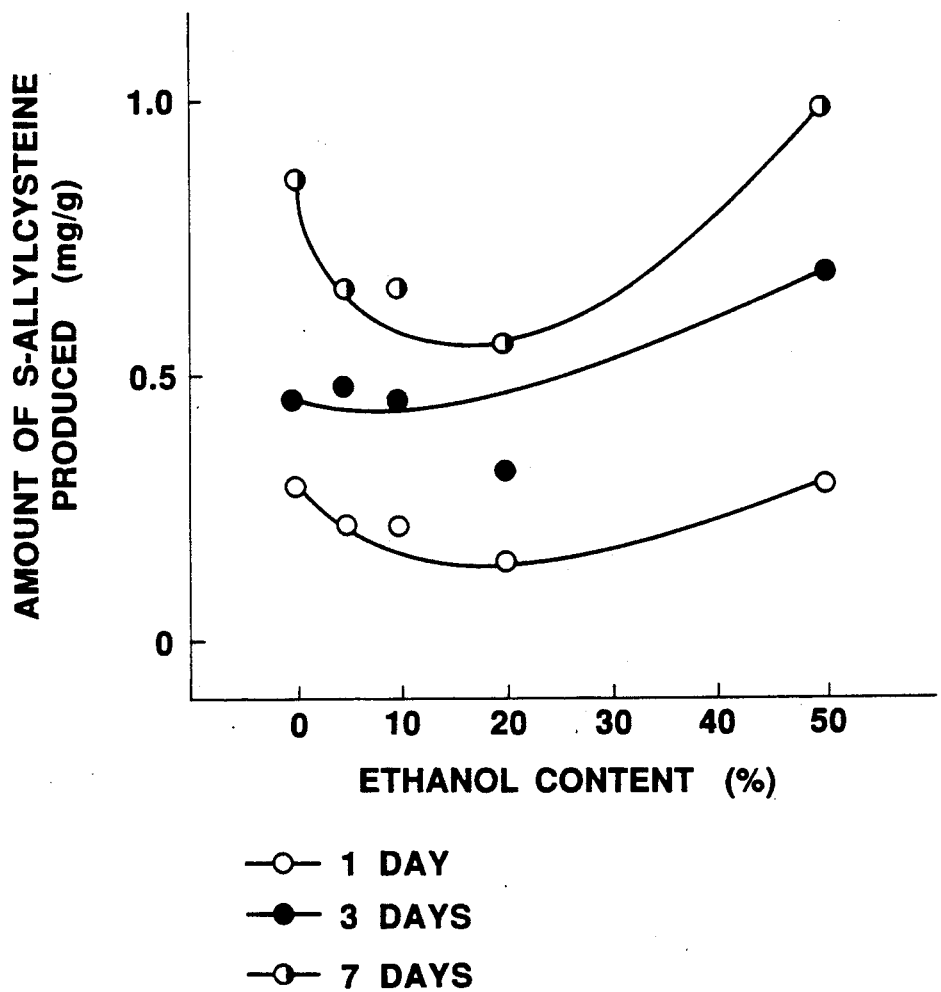
FIG. 3 is a diagram showing the amount of S-allylcysteine produced from garlic versus the content of ethanol.

The results are shown in FIG. 3.

EXAMPLE 4

To 47 grams of frozen elephant garlic was added 140 ml of water. The mixture was homogenized for about 3 minutes in a blender. The mixture was passed through a gauze filter and the filtrate was adjusted to pH 9.0 using 6 N NaOH. A test tube was charged with 10 ml of the filtrate, to which 25 mg of cysteine was added. The contents were fully agitated. As a control, another test tube was charged with 10 ml of the filtrate to which no cysteine was added. The test tubes were closed with plugs and allowed to stand at 37° C. for several days. Samples were taken out after 0, 3 and 5 days from the cysteine addition. The amount of S-allylcysteine produced was quantitatively determined by HPLC using a post column method.

Figure 4:
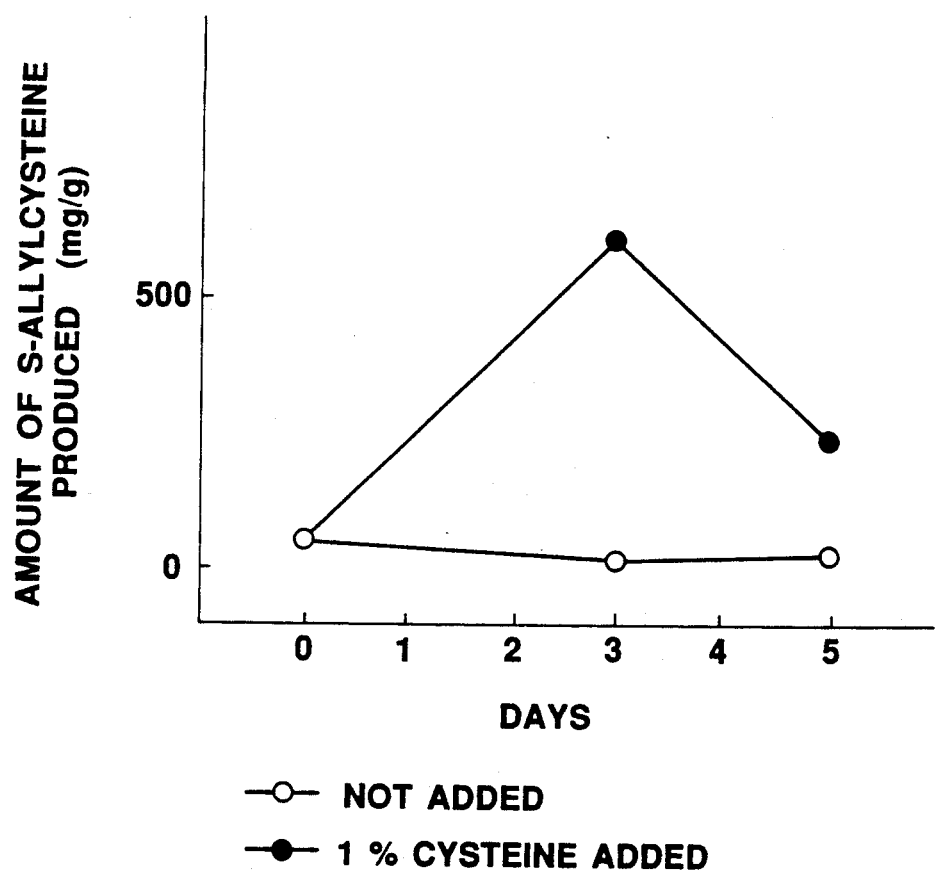
FIG. 4 is a diagram showing the amount of S-allylcysteine produced from elephant garlic.

The results are shown in FIG. 4.

Although some preferred embodiments have been described, many modifications and variations may be made thereto in the light of the above teachings. It is therefore to be understood that within the scope of the appended claims, the invention may be practiced otherwise than as specifically described.

I claim:

1. A method of preparing a composition comprising an extract of an Allium genus plant and S-allylcysteine comprising the steps of:

adding at least one polar solvent selected from the group consisting of water, lower aliphatic alcohols, and mixtures of water and a lower aliphatic alcohol to an Allium genus plant to obtain an extract liquid from the plant;

adding cysteine to the polar solvent, the mixture of the polar solvent and the plant under extraction or the extract liquid to convert the cysteine into S-allylcysteine in the extract liquid by adjusting the pH of the extract liquid to 7 to 12; and collecting the extract liquid containing the extract of the plant and S-allylcysteine.

2. The method of claim 1 wherein cysteine is added to the extract liquid collected.

3. The method of claim 1 wherein the polar solvent is water.

4. The method of claim 1 wherein the polar solvent is a low aliphatic alcohol in water.

5. The method of claim 1 wherein the step of causing the cysteine to convert into S-allylcysteine includes maintaining the liquid at room temperature to 50° C.

6. The method of claim 1, wherein the extract liquid is adjusted to pH 8 to 10.

7. The method of claim 1, wherein the extract liquid is adjusted to a temperature of 30° to 50° C.

* * * * *